(12) United States Patent
Music

(10) Patent No.: US 7,819,837 B2
(45) Date of Patent: Oct. 26, 2010

(54) DEVICE FOR CONTROLLING FLOW RATE OF ASPIRATED FLUIDS

(75) Inventor: Douglas E. Music, Wildwood, MO (US)

(73) Assignee: Bausch & Lomb Incorporated, Rochester, NY (US)

( * ) Notice: Subject to any disclaimer, the term of this patent is extended or adjusted under 35 U.S.C. 154(b) by 137 days.

(21) Appl. No.: 12/332,782

(22) Filed: Dec. 11, 2008

(65) Prior Publication Data

US 2010/0152656 A1    Jun. 17, 2010

(51) Int. Cl.
*A61M 1/00* (2006.01)
*A61M 37/00* (2006.01)

(52) U.S. Cl. .............................. 604/31; 604/30; 604/35; 604/118; 604/119; 604/131

(58) Field of Classification Search .................... 604/30, 604/31, 35, 118–120; 417/350, 351, 323, 417/336, 396
See application file for complete search history.

(56) References Cited

U.S. PATENT DOCUMENTS

| | | | |
|---|---|---|---|
| 5,499,969 A | 3/1996 | Beuchat | |
| 5,562,612 A | 10/1996 | Fox | |
| 5,685,821 A * | 11/1997 | Pike | 600/118 |
| 6,719,011 B2 | 4/2004 | Cull et al. | 138/37 |
| 6,752,795 B2 | 6/2004 | Cull | 604/323 |
| 7,217,257 B2 | 5/2007 | Cull et al. | 604/118 |
| 2004/0039351 A1 | 2/2004 | Barrett | 604/272 |
| 2004/0193099 A1 * | 9/2004 | MacMahon et al. | 604/30 |
| 2005/0118048 A1 | 6/2005 | Traxinger | |
| 2006/0135974 A1 | 6/2006 | Perkins | 606/169 |
| 2008/0294095 A1 | 11/2008 | Zacharias | 604/65 |

FOREIGN PATENT DOCUMENTS

EP      0 601 313 A2    6/1994

OTHER PUBLICATIONS

International Search Report (PCTISA/210) and Written Opinion (PCT/ISA/237) mailed on Mar. 3, 2010.

* cited by examiner

*Primary Examiner*—Nicholas D Lucchesi
*Assistant Examiner*—Leah Stohr
(74) *Attorney, Agent, or Firm*—Jeffrey B. Powers

(57) ABSTRACT

A flow control device includes a housing having a motor chamber and a pump chamber. The motor chamber has an outlet for communication with a fluid collection device, and an inlet for communication with an aspiration line through which fluids are delivered into the motor chamber. First and second motor rotors are rotatably disposed in a flow path between the inlet and the outlet in the motor chamber, and a drive shaft is coupled to the first motor rotor. The pump chamber has an outlet for infusing fluid to a surgical site, and an inlet through which infusion fluids are delivered into the pump chamber. First and second pump rotors are rotatably disposed in a flow path between the inlet and the outlet in the pump chamber, where the first pump rotor is coupled to the drive shaft. The drive shaft drives the pump rotors at the same speed as the motor rotors, such that any surge in aspiration flow induces a similar surge in infusion flow.

17 Claims, 2 Drawing Sheets

DEVICE FOR CONTROLLING FLOW RATE OF ASPIRATED FLUIDS

FIELD

The present disclosure relates to control of fluid flow into and out of a surgical site, and more particularly to the control of aspirated fluid flow in ophthalmic microsurgical systems.

BACKGROUND

This section provides background information related to the present disclosure which is not necessarily prior art.

During ophthalmic microsurgery, a surgeon may introduce the flow of fluids into an operative site in an eye, and fluids may be aspirated from the operative site utilizing flow control devices for collecting aspirated fluids. However, it is important to prevent over-pressurizing or collapsing the eye to avoid trauma to the retina. The introduction of fluids and application of vacuum for aspirating fluids from the eye may accordingly pose certain risks. However, where vacuum-based systems are employed, aspiration flow rate is difficult to measure or to timely infer from the vacuum level. Additionally, changes in the vacuum applied, the aspiration flow rate and the infusion fluid pressure and flow rate may result in pressure variations within the eye. This makes the control of intraocular pressure and fluid flow into and out of the eye very desirable.

SUMMARY

This section provides a general summary of the disclosure, and is not a comprehensive disclosure of its full scope or all of its features. The present disclosure relates to a flow control device for balancing fluid flow into and out of a surgical site, especially an eye. According to one aspect of the present disclosure, a flow control device includes a housing having a motor chamber and a pump chamber. The motor chamber has an outlet in communication with a fluid collection device, and an inlet in communication with an aspiration line through which fluids are delivered into the motor chamber. First and second motor rotors are rotatably disposed in the flow path between the inlet and the outlet in the motor chamber. At least one motor rotor is coupled to the end of a drive shaft. The pump chamber has an outlet for infusing fluid to a surgical site, and an inlet through which infusion fluids are delivered into the pump chamber. First and second pump rotors are rotatably disposed in the flow path between the inlet and the outlet in the pump chamber. At least one pump rotor is coupled to a drive shaft that is also coupled to a motor rotor. The drive shaft drives the pump rotor at the same speed as the motor rotor, such that any surge in aspiration flow induces a similar surge in infusion flow.

Further areas of applicability will become apparent from the description provided herein. The description and specific examples in this summary are intended for purposes of illustration only and are not intended to limit the scope of the present disclosure.

BRIEF DESCRIPTION OF THE DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Figure 1:
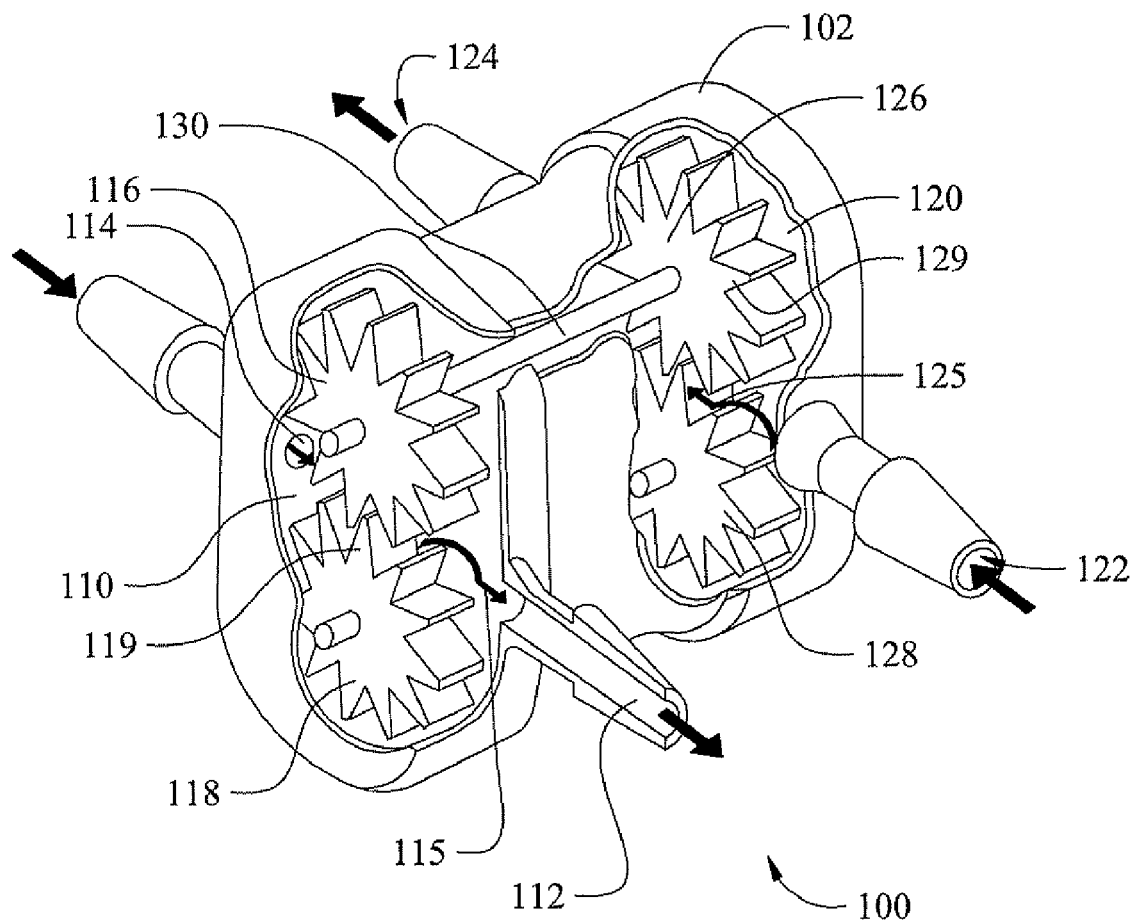
FIG. 1 is a perspective cut-away view of one embodiment of a flow control device for balancing fluid flow into and out of a surgical site, in accordance with the principles of the present disclosure.

Example embodiments will now be described more fully with reference to the accompanying drawings. The foregoing description of the embodiments has been provided for purposes of illustration and description. It is not intended to be exhaustive or to limit the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention.

In the various embodiments, a flow control device is provided for balancing fluid flow into and out of a surgical site, such as an eye. Ophthalmic microsurgery systems typically supply an aspirant fluid, such as a balanced salt solution (BSS), for example, to a surgical site via an infusion line. Fluids are typically aspirated from the surgical site through an aspiration line, which may be connected to a fluid collection cassette or collection bag. Ophthalmic microsurgery systems may employ a vacuum or other suitable aspiration source in communication with the aspiration line to establish a vacuum for urging the aspiration of fluid from a surgical site. A flow sensor may also be used in an attempt to monitor the rate that fluid is being aspirated from the surgical site. However, any surge in the aspiration flow due to a change in vacuum level will result in a change in the intraocular eye pressure, which could cause trauma or injury to the eye. Similarly, any surge in the infusion line will result in an increase in the intraocular eye pressure, which could cause trauma or injury to the eye.

To address these concerns, a flow control device 100 is configured to be placed in line with and connected to an aspiration line, and also in line with and connected to an infusion line to the surgical site. The flow control device 100 is preferably positioned in the infusion and aspiration lines proximal to a surgical handpiece for regulating fluid flow. It is also possible that flow control device 100 could be incorporated with a surgical handpiece, such that the flow control device can be placed very close to the surgical site. The infusion fluid flow into the eye and the aspiration fluid flow out of an eye is regulated or controlled by the flow control device 100, to thereby prevent any surge-induced pressure changes that could affect the intraocular eye pressure in the eye.

Generally, the aspiration flow control device includes a housing having a motor chamber and a pump chamber. The motor chamber has an outlet in communication with a fluid collection device, and an inlet in communication with an aspiration line through which fluids are delivered into the motor chamber. First and second motor rotors are rotatably disposed in the flow path between the inlet and the outlet in the motor chamber. At least one motor rotor is coupled to the end of a drive shaft. The pump chamber has an outlet for infusing fluid to a surgical site, and an inlet through which infusion fluids are delivered into the pump chamber. First and second pump rotors are rotatably disposed in the flow path between the inlet and the outlet in the pump chamber. At least one pump rotor is coupled to a drive shaft that is coupled to a motor rotor. The drive shaft drives the pump rotor at the same speed as the motor rotor, such that any surge in aspiration flow induces a similar surge in infusion flow.

Referring to FIG. 1, one embodiment of a fluid flow control device 100 for providing balanced fluid flow into and out of a surgical site is shown. As shown in FIG. 1, the fluid flow balancing device 100 includes a housing 102 having a motor chamber 110 and a pump chamber 120 that are disposed within the housing 102 adjacent each other. The motor chamber 110 has an outlet 112 for communication with a fluid collection device or vacuum source (not shown) via an aspiration line (also not shown), and an inlet 114 for communication with an aspiration line or outlet of a surgical handpiece through which fluids from a surgical site are delivered to the motor chamber 110. The pump chamber 120 has an outlet 124 for communication with an infusion line or inlet of a surgical handpiece (not shown) for supplying fluid to a surgical site, and an inlet 122 for attachment to an infusion line through which infusion fluids are delivered to the pump chamber 120. The inlet and outlet to the motor chamber 110 and the inlet and outlet to the pump chamber 120 may further comprise a tubing barb configured for connection with known surgical tubing.

A first motor rotor 116 and a second motor rotor 118 are rotatably disposed within the motor chamber 110, and positioned in the flow path 115 between the inlet 114 and the outlet 112 in the motor chamber 110. The first motor rotor 116 and second motor rotor 118 are positioned relative to each other such that at least one rotor blade 119 of both motor rotors overlap in the region of a flow path 115 between the inlet 114 and the outlet 112.

A first pump rotor 126 and a second pump rotor 128 are rotatably disposed within the pump chamber 120, and positioned in an infusion flow path 125 between an inlet 122 and an outlet 124 in the pump chamber 120. The first pump rotor 126 and second pump rotor 128 are positioned relative to each other such that at least one rotor blade 129 of both pump rotors overlap in the region of the flow path 125 between the inlet 122 and the outlet 124 of the pump chamber 120.

The flow control device 100 further includes a drive shaft 130 having a first end coupled to the first motor rotor 116 and a second end coupled to the first pump rotor 126. Fluid flowing between the inlet 114 and outlet 112 of the motor chamber 110 cause the first motor rotor 116 to rotate the drive shaft 130. The drive shaft 130 drives the first pump rotor 126 at the same rotational speed as the first motor rotor 116, such that any surge in aspiration fluid flow through the motor chamber 110 induces a similar surge in infusion fluid flow through the pump chamber 120. This accordingly reduces the risk of surge-induced pressure changes in the operative site. Similarly, any restriction that reduces the rate of aspirated fluid flow through the motor chamber 110 will reduce the speed of the pump rotors 126 and 128, to thereby reduce the risk of over-pressure in the operative site.

As shown in FIG. 1, the first and second motor rotors 116 and 118 are arranged generally parallel with the first and second pump rotors 126 and 128. Additionally, the first motor rotor 116 and first pump rotor 126 are axially aligned, and the second motor rotor 118 and second pump rotor 128 are axially aligned. Both the motor rotors 116, 118 and pump rotors 126, 128 are comprised of a generally paddle-wheel shaped configuration. In both the motor rotors 116, 118 and pump rotors 126 and 128, the overlap between the first rotor blades and second rotor blades results in the first and second rotors rotating at substantially the same rotational speed.

In operation, the motor rotors 116 and 118 act similarly to a turbine within a rotary engine, and are used to extract energy from a fluid flow 115 that flows past the motor rotors. The energy extracted from the fluid flow results in the rotation of the motor rotor 116, and the rotation of drive shaft 130. Because the first and second motor rotors 116 and 118 overlap in the region of the flow path (e.g.—their rotor blades overlap and contact each other), the first and second motor rotor blades each rotate at substantially the same rotational speed (rotations per minute). Similarly, when a decrease in the rate of aspirated fluid flow through the motor chamber 110 occurs, the fluid within the motor chamber 110 provides some resistance to the rotation of the motor rotors 116 and 118, which slows the rotor rotation. This reduced rotation in turn reduces the rotation of the pump rotors, to thereby reduce the flow of infusion fluid to the operative site and lessen the risk of unwanted increased intraocular pressure in the eye being operated on. The flow control device 100 may optionally include a bypass valve (not shown) on the pump stage that allows volume flow of infusion fluids to the operation site unrestricted by the rotors.

While FIG. 1 shows the motor rotors 116 and 118 positioned to overlap each other in the region of the flow path 115 that impinges on the rotor blades 119, in an alternate construction or embodiment, the rotor blades 119 may not overlap each other. For example, the rotors may be sufficiently spaced apart so that the rotor blades cannot contact each other, but positioned such that each rotor extends equally into the region of the flow path that impinges on the rotor blades.

Figure 2:
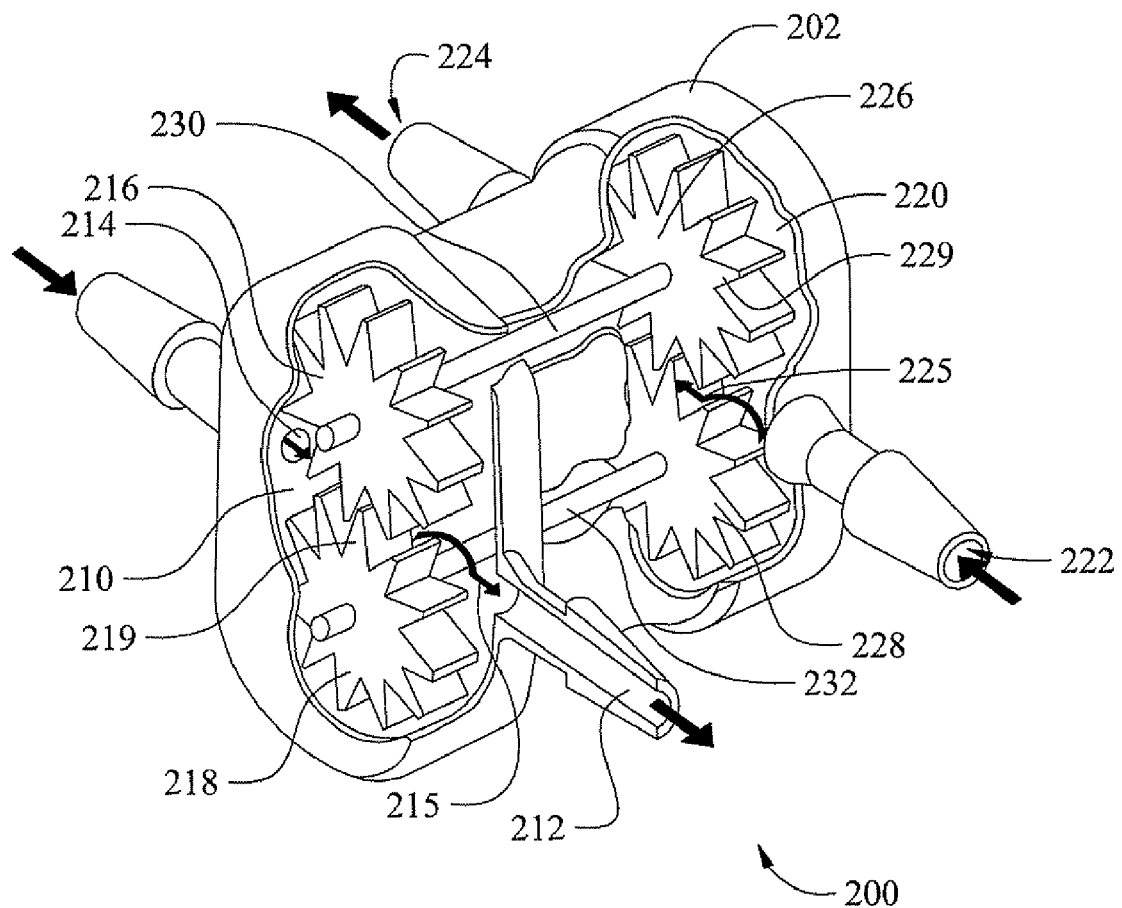
FIG. 2 is a perspective cut-away view of a second embodiment of a flow control device for balancing fluid flow into and out of a surgical site, in accordance with the principles of the present disclosure.

In one alternate embodiment shown in FIG. 2, the first motor rotor 216 and second motor rotor 218 are respectively coupled to a first drive shaft 230 and a second drive shaft 232, where the first and second drive shafts are further coupled to first and second pump rotors 226 and 228. The fluid flow 215 impinging on the motor rotor blades cause the motor rotors 216 and 218 to rotate, where each motor rotor rotates a corresponding drive shaft 230 or 232. In this alternate construction, the motor rotor blades 219 and pump rotor blades 229 may not overlap with each other.

The alternate embodiment shown in FIG. 2 comprises a housing 202 having a motor chamber 210 and a pump chamber 220 disposed therein, with two drive shafts 230 and 232 extending therebetween. The motor chamber 210 has an outlet 212 in communication with a fluid collection device (not shown), and an inlet 214 in communication with an aspiration line through which fluids from a surgical site are delivered to the motor chamber 210. The pump chamber 220 has an outlet 224 in communication with an infusion line (not shown) for supplying fluid to a surgical site, and an inlet 222 through which infusion fluids are delivered to the pump chamber 220. A first motor rotor 216 and a second motor rotor 218 are rotatably disposed within the motor chamber 210, and positioned in the flow path 215 between the inlet 214 and the outlet 212 in the motor chamber 210. A first pump rotor 226 and a second pump rotor 228 are rotatably disposed within the pump chamber 220, and positioned in the flow path 225 between the inlet 222 and the outlet 224 in the pump chamber 220. A first drive shaft 230 has one end coupled to the first motor rotor 216 and an opposite end coupled to the first pump rotor 226. A second drive shaft 232 has a one end coupled to the second motor rotor 218 and an opposite end coupled to the second pump rotor 228. Fluid flowing between the inlet 214 and outlet 212 of the motor chamber 210 causes the first and second motor rotors 216 and 218 to rotate the first and second drive shafts 230 and 232. Each drive shaft 230 and 232 drives its pump rotor at the same rotational speed as the respectively coupled motor rotor, such that any surge in aspiration fluid flow through the motor chamber induces a similar surge in infusion fluid flow, to thereby reduce the risk of surge-induced pressure changes in the operative site.

From the above, it may be appreciated that the present invention provides an improvement to aspiration fluid flow control, to thereby control the flow rate of fluid aspirated from a surgical site. The present invention is illustrated herein by example, and various modifications may be made by a person of ordinary skill in the art. It is believed that the operation and construction of the present invention will be apparent from the foregoing description. While the apparatus and methods shown or described above have been characterized as being preferred, various changes and modifications may be made therein without departing from the spirit and scope of the invention as defined in the following claims.

What is claimed is:

1. An ophthalmic surgical flow control device for balancing fluid flow into and out of a surgical site, comprising:
   a housing forming a motor chamber adjacent a pump chamber;
   the motor chamber having an outlet for communication with a fluid collection device and a source of aspiration, and an inlet for communication with an aspiration line through which fluids from the surgical site are delivered to the motor chamber;
   the pump chamber having an outlet for communication with an infusion line for supplying fluid to the surgical site, and an inlet for communication with a source of infusion fluid;
   a first motor rotor and a second motor rotor rotatably disposed within the motor chamber, and positioned in an aspiration flow path between the motor chamber inlet and outlet in the motor chamber, wherein the first and second motor rotors are positioned relative to each other such that at least one blade of both motor rotors overlap in a region of the aspiration flow path;
   a first pump rotor and a second pump rotor rotatably disposed within the pump chamber, and positioned in an infusion flow path between the pump chamber inlet and the outlet, wherein the first and second pump rotors are positioned relative to each other such that at least one blade of both pump rotors overlap in a region of the infusion path;
   a drive shaft having a first end coupled to the first motor rotor and a second end coupled to the first pump rotor; and
   wherein fluid flowing between the inlet and outlet of the motor chamber causes the first motor rotor to rotate the drive shaft, whereby the drive shaft drives the first pump rotor at the same rotational speed as the first motor rotor such that any surge in aspiration fluid flow through the motor chamber induces a similar surge in infusion fluid flow to the operative site, to thereby reduce the risk of surge-induced pressure changes in the operative site.

2. The flow control device of claim 1, wherein the drive shaft drives the first pump rotor at the same rotational speed as the first motor rotor such that any decrease in aspiration fluid flow through the motor chamber induces a similar decrease in infusion fluid flow to the operative site.

3. The flow control device of claim 1, wherein the first and second motor rotors are arranged generally parallel with the first and second pump rotors.

4. The flow control device of claim 3, wherein the first motor rotor and first pump rotor are axially aligned, and the second motor rotor and second pump rotor are axially aligned.

5. The flow control device of claim 4, wherein the motor rotors and pump rotors are comprised of a generally paddlewheel shaped configuration.

6. The flow control device of claim 4, wherein the overlap between first motor rotor blades and second motor rotor blades results in the first and second motor rotors rotating at substantially the same rotational speed.

7. The flow control device of claim 4, wherein the overlap between first pump rotor blades and second pump rotor blades results in the first and second pump rotors rotating at substantially the same rotational speed.

8. The flow control device of claim 4, wherein the motor rotors extract energy from the fluid flowing between the inlet and outlet of the motor chamber, to thereby rotate the drive shaft.

9. The flow control device of claim 1, wherein the inlet and outlet to the motor chamber and the inlet and outlet to the pump chamber further comprise a tubing barb configured for connection to surgical tubing.

10. A flow control device for balancing fluid flow into and out of a surgical site, comprising:
    a housing having a motor chamber disposed therein, and a pump chamber disposed therein adjacent to the motor chamber;
    the motor chamber having an outlet for communication with a fluid collection device, and an inlet in communication with an aspiration line through which fluids from a surgical site are delivered to the motor chamber;
    the pump chamber having an outlet for communication with an infusion line for supplying fluid to a surgical site, and an inlet through which infusion fluids are delivered to the pump chamber;
    a first motor rotor and a second motor rotor rotatably disposed within the motor chamber, and positioned in a flow path between the inlet and the outlet in the motor chamber;
    a first pump rotor and a second pump rotor rotatably disposed within the pump chamber, and positioned in a flow path between the inlet and the outlet in the pump chamber;
    a first drive shaft having a first end coupled to the first motor rotor and a second end coupled to the first pump rotor;
    a second drive shaft having a first end coupled to the second motor rotor and a second end coupled to the second pump rotor; and
    wherein fluid flowing between the inlet and outlet of the motor chamber causes the first and second motor rotors to rotate the first and second drive shafts, whereby each drive shaft drives one of the pump rotors at the same rotational speed as a respectively coupled motor rotor, such that any surge in aspiration fluid flow through the motor chamber induces a similar surge in infusion fluid flow through the pump chamber, to thereby reduce the risk of surge-induced pressure changes in the surgical site.

11. The flow control device of claim 10, wherein the first drive shaft drives the first pump rotor at the same rotational speed as the first motor rotor such that any decrease in aspiration fluid flow through the motor chamber induces a similar decrease in infusion fluid flow to the operative site.

12. The flow control device of claim 10, wherein the first and second motor rotors are arranged generally parallel with the first and second pump rotors.

13. The flow control device of claim 12, wherein the first motor rotor and first pump rotor are axially aligned, and the second motor rotor and second pump rotor are axially aligned.

14. The flow control device of claim 13, wherein the motor rotors and pump rotors are comprised of a generally paddle-wheel shaped configuration.

15. The flow control device of claim 13, wherein an overlap between first motor rotor blades and second motor rotor blades results in the first and second motor rotors rotating at substantially the same rotational speed.

16. The flow control device of claim 13, wherein an overlap between first pump rotor blades and second pump rotor blades results in the first and second pump rotors rotating at substantially the same rotational speed.

17. The flow control device of claim 10, wherein the inlet and outlet to the motor chamber and the inlet and outlet to the pump chamber further comprise a tubing barb configured for connection to surgical tubing.

* * * * *